United States Patent [19]

Culbert

[11] Patent Number: Plant 5,719

[45] Date of Patent: Apr. 15, 1986

[54] CHRYSANTHEMUM PLANT NAMED ILLINI SUMMER

[75] Inventor: John R. Culbert, Clinton, Ill.

[73] Assignee: University of Illinois, Chicago, Ill.

[21] Appl. No.: 660,056

[22] Filed: Oct. 12, 1984

Related U.S. Application Data

[63] Continuation of Ser. No. 488,011, Apr. 25, 1983, abandoned.

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Illini Summer, characterized by its flat capitulum form, single anemone capitulum type, bright yellow ray florets and somewhat deeper yellow mature disc florets, 45–55 mm. diameter across face of capitulum, short and compact growth habit, and its outstanding keeping quality for both form and color.

2 Drawing Figures

This is a continuation of application Ser. No. 488,011, filed Apr. 25, 1983 now abandoned.

The present invention comprises a new and distinct cultivar of *Chrysanthemum morifolium,* Ramat., named Illini Summer.

Illini Summer is a product of a planned breeding program which had the objective of creating new chrysanthemum cultivars with single anemone capitulum type with anemone center, bright yellow ray floret color, 9 week response, and with the ability to produce commercially acceptable quality in year round pot mum programs. Such traits in combination were not present in previously available commercial cultivars.

Illini Summer was originated from a hybridization made in a controlled breeding program in Champagne, Ill. in 1974. Illini Summer was discovered and selected as one flowering plant within thr progency of the selected parentage by John R. Culbert in May 1975 in a controlled environment in Champagne, Ill., and subsequently given the code name FP-Ill-75-47-YS.

The first act of asexual reproduction of Illini Summer was accomplished when vegetative cuttings were taken from the initial selection in October, 1975 in a controlled environment in Champagne, Ill. by a technician working under formulations established and supervised by John R. Culbert. Horticultural examination of selected units initiated Feb. 7, 1976 has demonstrated that the combination of characteristics as herein disclosed for Illini Summer are firmly fixed and are retained through successive generations of asexual reproduction.

Illini Summer has not been observed under all possible environmental conditions. The phenotype may vary significantly with variations in environment such as temperature, light intensity, and day length. The following observations, measurements and comparisons describe plants grown in Champagne and West Chicago, Ill. and Parrish, Fla. under greenhouse conditions which approximate those generally used in commercial practice.

The following traits have been repeatedly observed and are determined to be basic characteristics of Illini Summer, which in combination distinguish this chrysanthemum as a new and distinct cultivar:

1. Flat capitulum form.
2. Single anemone capitulum type.

3. The anemone disc florets are more developed and pronounced under certain conditions. Under high temperatures they are smaller and less pronounced than under low temperatures.
4. Bright yellow ray florets.
5. Small flower diameter, with the diameter across face of the capitulum being 45–55 mm.
6. Yellow-green (immature) to yellow (mature) disc florets.
7. Semi-upright branching pattern.
8. Short pot plant height of about 130–170 mm. from edge of the pot.
9. Outstanding keeping quality for both form and color.

The accompanying photographic drawings show typical inflorescence and foliage characteristics of Illini Summer, with colors being as nearly true as possible with illustrations of this type. Sheet 1 is a color photograph of Illini Summer, and sheet 2 is a black and white print of the underside of typical foliage of Illini Summer taken at various stages of growth.

In the following description color references are made to The Royal Horticultural Society Colour Chart. The color value were determined between 8:00–9:00 A.M. on Apr. 25, 1983 under 2000–3000 foot candles at Parrish, Fla.

Classification:

*Botanical.*—*Chrysanthemum morifolium,* Ramat., cv Illini Summer.

*Commercial.*—Pot mum.

I. Inflorescence:

A. *Capitulum.*—Form: Flat; rays and cushion are in good proportion; cushion is well defined and rounded and maintains form; approximately 30–40 ray florets arranged in 2 rows. Type: Single anemone. Diameter Across Face: 45–55 mm. when produced on pinched plants. Number: 15 to 22 flowers per plant.

B. *Corolla of ray florets.*—Color (general tonality from a distance of three meters): Bright yellow. Color (lower surface): 4B. Color (upper surface): 3A fading to 6C.

C. *Corolla of disc florets.*—Color (mature): 9A. Color (immature):150A.

D. *Reproductive organs.*—Androecium: Present in disc florets only — Many. Gynoecium: Present in both ray and disc florets — Many.

II. Plant:

A. *General appearance.*—Short, compact and strong growth habit; height, 130–170 mm; small foliage.

B. *Foliage.*—Color (abaxial): 147B. Color (adaxial): 147A. Shape: Ovate, deeply lobed and serrate.

C. *Response.*—Consistently an early 9 week response.

I claim:

1. A new and distinct form of chrysanthemum plant named Illini Summer, as described and illustrated, and particularly characterized by its flat capitulum form, single anemone capitulum type, bright yellow ray florets and somewhat deeper yellow mature disc florets; 45–55 mm. diameter across face of capitulum; short and compact growth habit, and its outstanding keeping quality for both form and color.

* * * * *

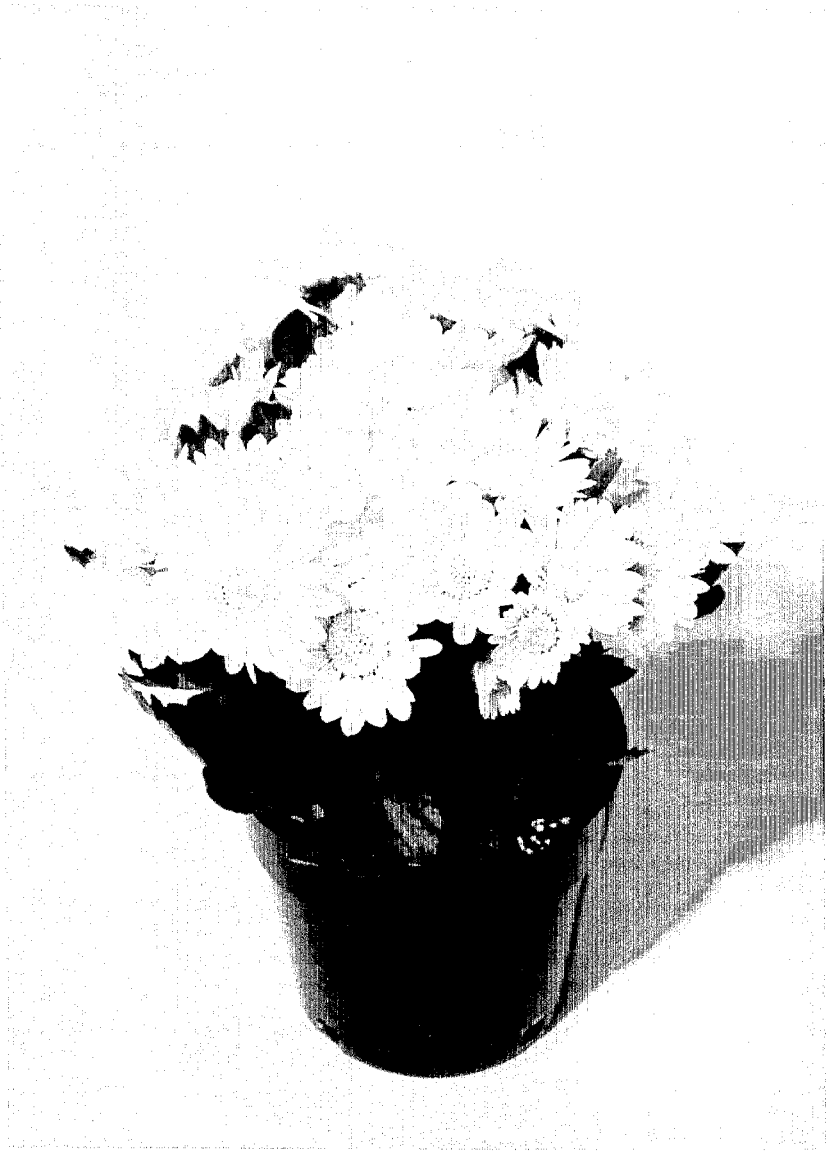

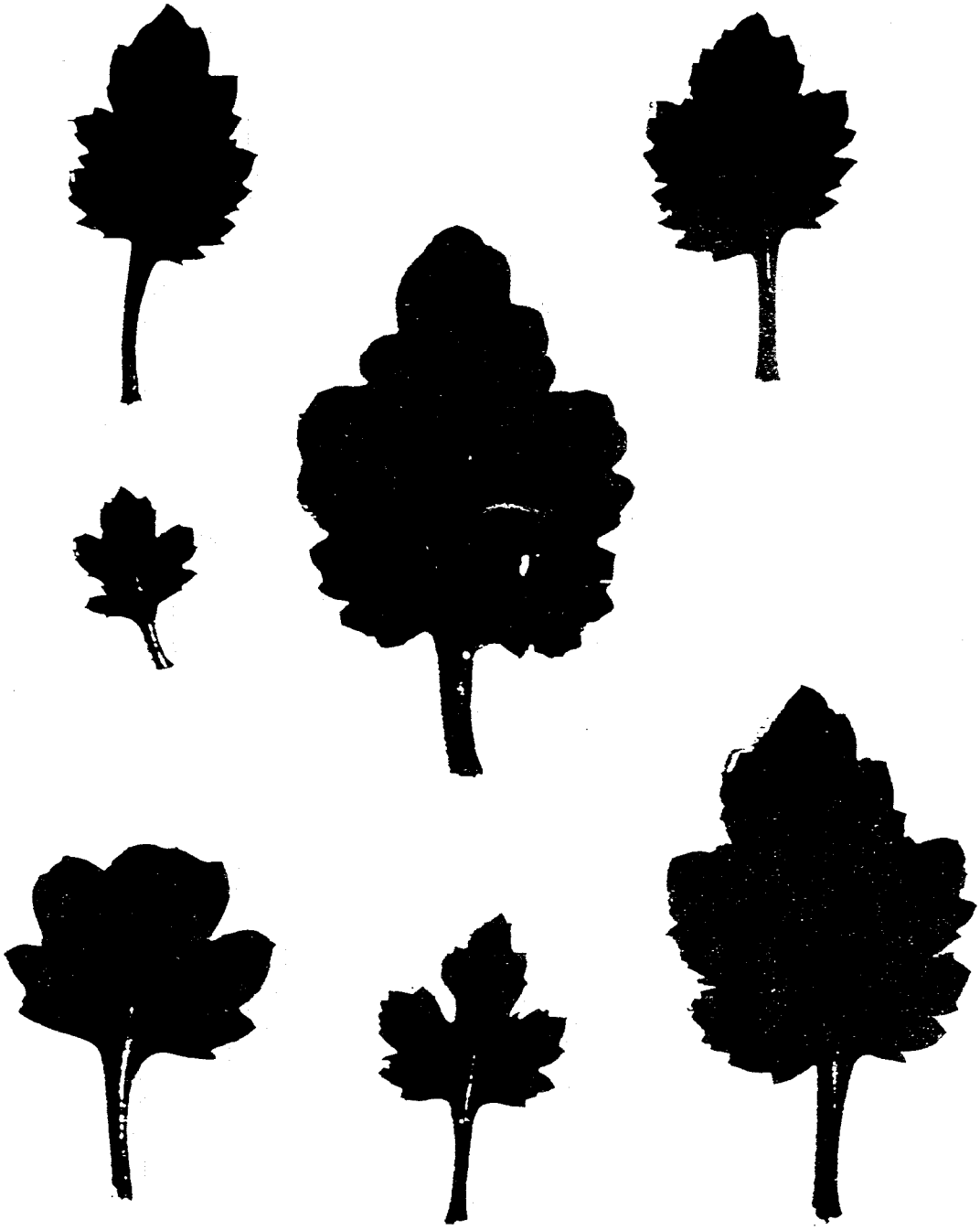
ILLINI SUMMER
(abaxial)